(12) United States Patent
Matsuzaki et al.

(10) Patent No.: US 9,097,244 B2
(45) Date of Patent: Aug. 4, 2015

(54) FLUID FEEDING PUMP, MEDICAL APPARATUS, AND AIR BUBBLE DETECTION METHOD FOR FLUID FEEDING PUMP

(75) Inventors: Takahiro Matsuzaki, Shiojiri (JP); Takeshi Seto, Chofu (JP); Kunio Tabata, Shoijiri (JP); Shinichi Miyazaki, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 374 days.

(21) Appl. No.: 13/595,987

(22) Filed: Aug. 27, 2012

(65) Prior Publication Data

US 2013/0052044 A1    Feb. 28, 2013

(30) Foreign Application Priority Data

Aug. 30, 2011  (JP) ................. 2011-186963

(51) Int. Cl.
*A61B 17/3203* (2006.01)
*F04B 13/02* (2006.01)
*F04B 43/04* (2006.01)
*F04B 17/03* (2006.01)
*F04B 45/047* (2006.01)

(52) U.S. Cl.
CPC ............. *F04B 13/02* (2013.01); *A61B 17/3203* (2013.01); *F04B 17/03* (2013.01); *F04B 43/046* (2013.01); *F04B 45/047* (2013.01)

(58) Field of Classification Search
CPC .......................... A61B 17/3203; F04B 43/046
USPC ................. 417/413.2; 604/48, 131, 151, 153; 606/159, 167
See application file for complete search history.

(56) References Cited

U.S. PATENT DOCUMENTS

| | | | |
|---|---|---|---|
| 6,375,299 B1 * | 4/2002 | Foster et al. | ..................... 347/19 |
| 6,709,240 B1 | 3/2004 | Schmalz et al. | |
| 7,011,507 B2 | 3/2006 | Seto et al. | |
| 7,396,511 B2 * | 7/2008 | Fujii et al. | ..................... 422/562 |

(Continued)

FOREIGN PATENT DOCUMENTS

| | | |
|---|---|---|
| JP | 63-141750 | 6/1988 |
| JP | 2001-132646 | 5/2001 |

(Continued)

OTHER PUBLICATIONS

Cheng, G et al.; "Ferroelectric Properties of BiFeO3 Thin Films Prepared via a Simple Chemical Solution Deposition" Ferroelectrics, Taylor & Francis Aug. 2010, vol. 406, pp. 1481-1486, 1588.

*Primary Examiner* — Peter J Bertheaud
(74) *Attorney, Agent, or Firm* — Workman Nydegger (57) ABSTRACT

A fluid feeding pump which varies a volume of a pump chamber and thus feeds a fluid out of the pump chamber, includes: a piezoelectric element which accumulates electric charges inside when a voltage is applied, and which deforms according to an amount of accumulated electric charges and thus increases or decreases the volume of the pump chamber; a drive unit which applies a drive signal with a waveform increasing to a predetermined maximum voltage and then decreasing, and thus drives the piezoelectric element; and an air bubble determining unit which detects a current flowing through the piezoelectric element within a predetermined period after the drive signal is applied to the piezoelectric element, and thus determines whether there are air bubbles in the pump chamber or not.

9 Claims, 7 Drawing Sheets

(56) References Cited

U.S. PATENT DOCUMENTS

| | | | |
|---|---|---|---|
| 7,901,374 B2 * | 3/2011 | Seto et al. | 604/48 |
| 8,337,452 B2 * | 12/2012 | Seto et al. | 604/48 |
| 8,382,702 B2 * | 2/2013 | Uchida et al. | 604/67 |
| 8,506,584 B2 * | 8/2013 | Seto et al. | 606/167 |
| 8,652,091 B2 * | 2/2014 | Seto et al. | 604/48 |
| 8,794,931 B2 * | 8/2014 | Takahashi | 417/216 |
| 8,857,734 B2 * | 10/2014 | Kojima | 239/102.1 |
| 2002/0098122 A1 | 7/2002 | Singh et al. | |
| 2004/0013539 A1 | 1/2004 | Takagi et al. | |
| 2005/0019180 A1 | 1/2005 | Seto et al. | |
| 2005/0159639 A1 | 7/2005 | Skliar et al. | |
| 2007/0133968 A1 | 6/2007 | Kawamura et al. | |
| 2010/0177147 A1 | 7/2010 | Kusunoki et al. | |
| 2011/0112479 A1 | 5/2011 | Tomoyama et al. | |
| 2011/0208224 A1 * | 8/2011 | Kojima | 606/167 |
| 2011/0213396 A1 * | 9/2011 | Tabata et al. | 606/167 |
| 2013/0064683 A1 | 3/2013 | Oshima et al. | |

FOREIGN PATENT DOCUMENTS

| | | |
|---|---|---|
| JP | 2004-011535 | 1/2004 |
| JP | 2004-314459 | 11/2004 |
| JP | 2006-078334 | 3/2006 |
| JP | 2008-082202 | 4/2008 |
| JP | 2010-242764 | 10/2010 |
| JP | 2011-103930 | 6/2011 |
| JP | 2011-177330 | 9/2011 |
| SU | 1185226 | 10/1985 |

* cited by examiner

FLUID FEEDING PUMP, MEDICAL APPARATUS, AND AIR BUBBLE DETECTION METHOD FOR FLUID FEEDING PUMP

BACKGROUND

1. Technical Field

The present invention relates to a fluid feeding pump which feeds a fluid.

2. Related Art

A circulation pump which circulates a fluid through a channel is previously known. The circulation pump has a pump chamber with a variable volume. After the volume of the pump chamber is increased to suck a fluid into the pump chamber from the channel, the volume of the pump chamber is reduced to pressurize the fluid in the pump chamber. The fluid is thus fed into the channel from the pump chamber. Therefore, by increasing and decreasing the volume of the pump chamber, the fluid can be circulated through the channel.

In the case where air bubbles enter the pump chamber, when the volume of the pump chamber is reduced, the air bubbles are compressed and fluid is not pressurized. Therefore, the fluid cannot be fed. Thus, a technique of providing the circulation pump with a detection device for detecting air bubbles in the pump chamber and carrying out maintenance of the circulation pump to remove air bubbles from inside the pump chamber when the air bubbles are detected by the detection device, is proposed (JP-A-2010-242764).

However, the above technique has a problem that the circulation pump is increased in size because the detection device for detecting air bubbles needs to be provided separately in the circulation pump. The technique of feeding a fluid using the pump chamber is not limited to the circulation pump and is also used for a fluid ejection device which ejects a fluid after narrowing the fluid fed from a pump chamber, with an ejection nozzle. An increase in size of the device similarly takes place when the detection device is provided in the fluid ejection device.

SUMMARY

An advantage of some aspects of the invention is to provide a technique which enables detection of air bubbles in the pump chamber without increasing the size of the device.

An aspect of the invention is directed to a fluid feeding pump which increases a volume of a pump chamber to suck a fluid into the pump chamber and then reduces the volume of the pump chamber to feed the fluid from inside the pump chamber, including: a piezoelectric element which accumulates electric charges inside when a voltage is applied, and which deforms according to an amount of accumulated electric charges and thus increases or decreases the volume of the pump chamber; a drive unit which applies a drive signal with a waveform increasing to a predetermined maximum voltage and then decreasing, and thus drives the piezoelectric element; and an air bubble determining unit which detects a current flowing through the piezoelectric element within a predetermined period after the drive signal is applied to the piezoelectric element, and thus determines whether there are air bubbles in the pump chamber or not.

In the fluid feeding pump having this configuration according to the above aspect, when the drive signal is applied and the piezoelectric element is driven, the volume of the pump chamber is increased or decreased and the fluid is fed from the pump chamber. Also, by detecting the current flowing within the predetermined period after the drive signal is applied to the piezoelectric element, whether there are air bubbles in the pump chamber or not can be determined. To "detect the current flowing within the predetermined period" is not limited to detecting the current over the entire predetermined period. The current may be detected in a partial period of the predetermined period, or the current may be detected at a certain point in the predetermined period.

In the case where air bubbles are in the pump chamber, the present air bubbles collapse when the drive signal is applied to the piezoelectric element. Therefore, the way the piezoelectric element deforms is different, compared with the case where there are no air bubbles in the pump chamber. Consequently, the current waveform flowing through the piezoelectric element varies depending on whether there are air bubbles in the pump chamber or not. Therefore, by detecting the current flowing within the predetermined period after the drive signal is applied to the piezoelectric element, whether there are air bubbles in the pump chambers or not can be determined. Also, in such a determination of whether there are air bubbles or not, it suffices to detect the current flowing through the piezoelectric element. Therefore, a separate device for detecting air bubbles need not be provided in the fluid feeding pump. Thus, the fluid feeding pump can be small-sized and hence an apparatus in which the fluid feeding pump is installed can be small-sized as a whole.

In the fluid feeding pump according to the above aspect, the predetermined period for detecting the current flowing through the piezoelectric element may be a period from when the drive signal reaches the maximum voltage to when the application of the drive signal to the piezoelectric element is started, or may be a period after the drive signal reaches the maximum voltage to when the application of the drive signal to the piezoelectric element is started.

In the state where there are no air bubbles in the pump chamber, the current continues flowing through the piezoelectric element even when the drive signal reaches the maximum voltage. However, where air bubbles are in the pump chamber, the current stop flowing when the drive signal reaches the maximum voltage. Therefore, by detecting the current flowing through the piezoelectric element in the predetermined period starting when the drive signal reaches the maximum voltage or the predetermined period starting after the drive signal reaches the maximum voltage, whether there are air bubbles in the pump chamber or not can be determined. Also, in such a determination of whether there are air bubbles or not, a separate device for detecting air bubbles need not be provided in the fluid feeding pump. Therefore, the fluid feeding pump can be small-sized.

In the fluid feeding pump according to the above aspect, a drive signal such that an amount of voltage change to time is 0 when the maximum voltage is reached and the amount of voltage change increases with the lapse of time in a predetermined period after the maximum voltage is reached, may be applied to the piezoelectric element.

By doing so, for a while after the maximum voltage is reached, the voltage change of the drive signal is small. As the voltage of the drive signal changes, the current corresponding to the change speed is to flow through the piezoelectric element. Therefore, in order to detect the current flowing through the piezoelectric element based on whether there are air bubbles or not, a small voltage change of the drive signal is desirable. Thus, by achieving a small voltage change of the drive signal for a while after the drive signal reaches the maximum voltage, the current flowing in the predetermined period after the maximum voltage is reached can be detected accurately and therefore whether there are air bubbles or not can be determined accurately.

Also, in the fluid feeding pump according to the above aspect, whether there are air bubbles in the pump chamber or not may be detected by detecting a size of a predetermined frequency component of the current flowing through the piezoelectric element.

The fact that the current continues flowing even after the drive signal reaches the maximum voltage, means that the current smoothly changes and the influence thereof can be seen in the size of frequency components of the current waveform. In practice, as frequency components of the current waveform flowing through the piezoelectric element are analyzed in the case where there are air bubbles in the pump chamber and in the case where there are no air bubbles, there is a marked difference in the size of a predetermined frequency component. Therefore, by analyzing the frequency of the current waveform, or by detecting a predetermined frequency component with a filter, whether there are air bubbles in the pump chamber or not can be detected easily.

BRIEF DESCRIPTION OF THE DRAWINGS

The invention will be described with reference to the accompanying drawings, wherein like numbers reference like element.

DESCRIPTION OF EXEMPLARY EMBODIMENTS

Figure 1:
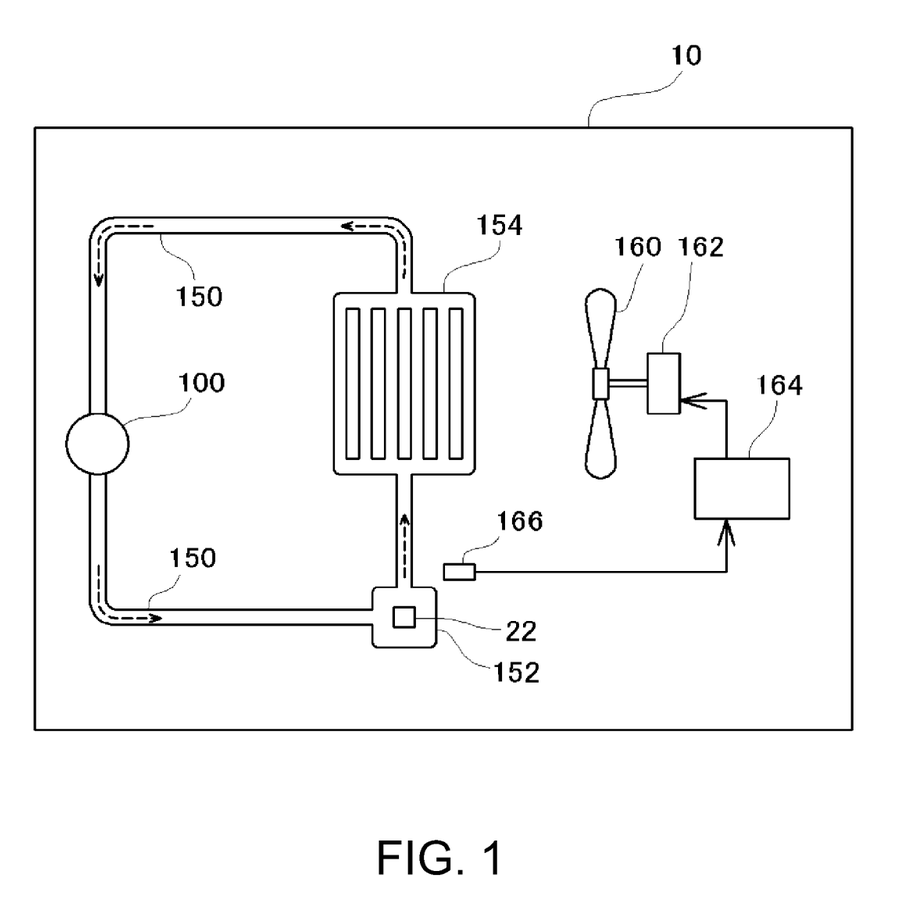
FIG. 1 is an explanatory view showing the configuration of a cooling device according to an embodiment.

Hereinafter, an embodiment will be described in the following order in order to clarify the contents of the invention.
A. Configuration of Cooling Device
B. Configuration of Fluid Feeding Pump
C. Operations of Fluid Feeding Pump
D. Principle of Detecting Air Bubbles
E. First Example
F. Second Example
A. Configuration of Cooling Device FIG. 1 is an explanatory view showing the configuration of a cooling device 10 according to this embodiment. As shown in FIG. 1, the cooling device 10 of this embodiment has a fluid channel 150 through which a fluid flows, a fluid feeding pump 100 which circulates the fluid through the fluid channel 150, and the like. On the way through the fluid channel 150, a heat receiving unit 152 which causes the fluid to absorb heat from a heat source 22 such as an electronic component, and a heat radiating unit 154 which radiates heat of the fluid are provided. The fluid channel 150, the heat receiving unit 152 and the heat radiating unit 154 form a channel configuration to circulate the fluid to the fluid feeding pump 100. In FIG. 1, the direction in which the fluid flows is indicated by broken-line arrows.

In the heat receiving unit 152, the fluid flows in contact with a thermally conductive member, not shown, which is made of a material with a high thermal conductivity such as metal. The thermally conductive member is in contact with a portion having the heat of the heat source 22. Therefore, the heat of the heat source 22 is transmitted to the fluid via the thermally conductive member and the heat source 22 is thus cooled down. The heat radiating unit 154 is a so-called radiator and radiates the heat of the fluid flowing through the heat radiating unit 154 into the air via plural radiating fins formed in the surface. Consequently, the fluid passing through the heat radiating unit 154 is returned in the cooled state to the fluid feeding pump 100.

The cooling device 10 of this embodiment is also equipped with a cooling promoting unit which promotes heat radiation by the heat radiating unit 154. This cooling promoting unit includes a cooling fan 160, a fan motor 162 which causes the cooling fan 160 to rotate, a motor control unit 164 which controls operations of the fan motor 162, a temperature sensor 166 and the like. The temperature sensor 166 is arranged near the heat source 22 and detects the temperature of the heat source 22 and outputs the detected temperature to the motor control unit 164. The motor control unit 164 controls operations of the fan motor 162 based on the detected temperature. For example, when the temperature detected by the temperature sensor 166 is high, the rotational speed of the fan motor 162 is increased to promote heat radiation by the heat radiating unit 154. Thus, the temperature of the fluid flowing out of the heat radiating unit 154 is lowered and the fluid with a lower temperature is supplied to the heat receiving unit 152. Consequently, the temperature of the heat source 22 can be lowered.

B. Configuration of Fluid Feeding Pump

Figure 2A:
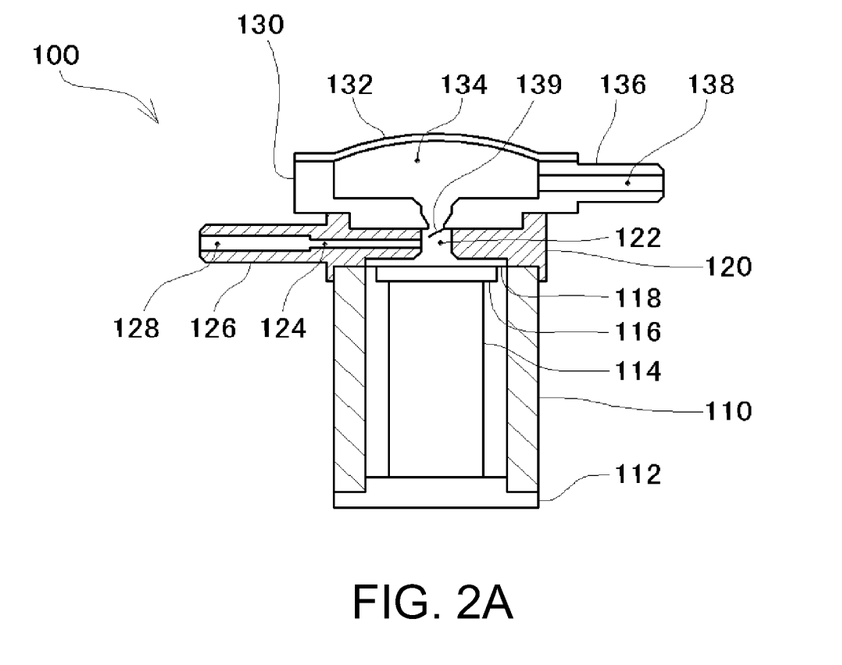
FIGS. 2A and 2B are explanatory views showing the configuration of a fluid feeding pump installed in the cooling device of the embodiment.
Figure 2B:
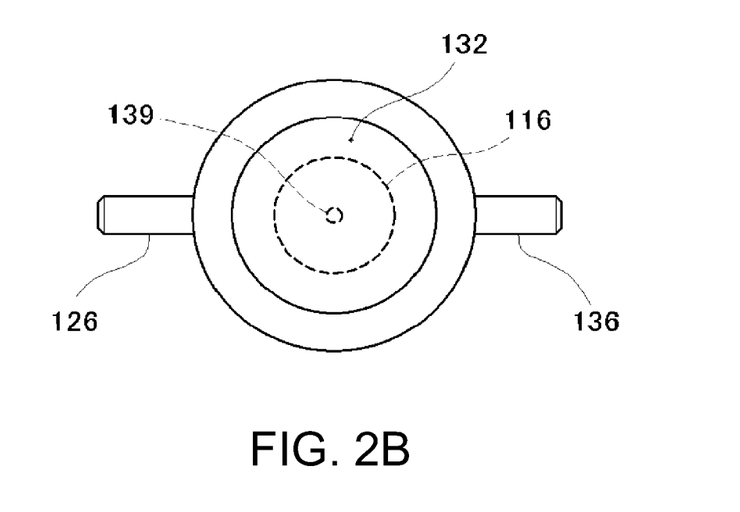

FIGS. 2A and 2B are explanatory views showing the structure of the fluid feeding pump 100 installed in the cooling device 10 of this embodiment. FIG. 2A shows a sectional view of the fluid feeding pump 100. FIG. 2B shows a top view of the fluid feeding pump 100. As shown in FIG. 2A, the fluid feeding pump 100 of this embodiment is configured roughly by three sections, that is, a piezoelectric element casing 110, a pump chamber block 120, and an inflow-side block 130.

Of these, the piezoelectric element casing 110 has a multilayer piezoelectric element 114 housed inside. A bottom plate 112 is firmly fixed to a bottom part of the piezoelectric element casing 110. A bottom part of the piezoelectric element 114 is adhered to the bottom plate 112. A reinforcing plate 116 is adhered to a top surface of the piezoelectric element 114. The piezoelectric element 114 has a property that when a positive voltage is applied, the piezoelectric element 114 expands according to the voltage value. The reinforcing plate 116 and the piezoelectric element casing 110 are polished so that a top surface of the reinforcing plate 116 and an end surface of the piezoelectric element casing 110 become flush with each other when no voltage is applied to the piezoelectric element 114. Therefore, as a positive voltage is applied to the piezoelectric element 114, the top surface of the reinforcing plate 116 slightly protrudes from the end surface of the piezoelectric element casing 110.

Moreover, on the top surface of the reinforcing plate 116 and the piezoelectric element casing 110, a circular plate-like diaphragm 118 made of a stainless steel sheet is adhered to the reinforcing plate 116 and the piezoelectric element casing 110.

In the pump chamber block 120, a shallow circular recessed portion opening toward a bottom side (toward the piezoelectric element casing 110) is formed. A central part of the recessed portion has a columnar penetrating shape. An inside diameter of the bottom side recessed portion is smaller than an outside diameter of the diaphragm 118. Therefore, as the pump chamber block 120 is placed on the piezoelectric element casing 110, the diaphragm 118 is sandwiched between an outside part of the recessed portion of the pump chamber block 120 and the piezoelectric element casing 110. In this state, the pump chamber block 120 is firmly attached to the piezoelectric element casing 110 by screwing or the like.

As the pump chamber block 120 is attached to the piezoelectric element casing 110, a pump chamber 122 is formed between the recessed portion formed on the bottom side of the pump chamber block 120 and the central penetrating portion of the recessed portion, and the diaphragm 118. When the piezoelectric element 114 expands or contracts, causing the diaphragm 118 to deform, the volume of the pump chamber 122 varies. An outlet connecting tube 126 is provided rising from a lateral surface of the pump chamber block 120. An outflow channel 128 is formed inside the outlet connecting tube 126. The pump chamber 122 connects to the outflow channel 128 via a thin channel 124. The fluid channel 150 shown in FIG. 1 is attached to the outlet connecting tube 126.

In the inflow-side block 130, a circular recessed portion opening toward a top side (opposite to the pump chamber block 120) is formed. At a central part of the recessed portion, a penetrating passage toward a bottom side (toward the pump chamber block 120) is formed. The recessed portion opening toward the top side is covered with a cover 132 which is flexible and has a high gas barrier property. An inflow-side buffer chamber 134 is formed between the cover 132 and the recessed portion of the inflow-side block 130. As a material of the cover 132, a composite material of a metal (for example, stainless steel, aluminum or the like) sheet and a resin, or a metal film or the like is desirable so that both flexibility and gas barrier property can be achieved. A passage connecting from the inflow-side buffer chamber 134 to the pump chamber 122 is gradually reduced in inside diameter. A check valve 139 made of a stainless steel sheet is provided at a portion of the passage's boundary with the pump chamber 122. Therefore, when the pressure in the pump chamber 122 is higher than the pressure in the inflow-side buffer chamber 134, the check valve 139 closes and a backflow of the fluid from the pump chamber 122 to the inflow-side buffer chamber 134 is prevented. On the other hand, when the pressure in the pump chamber 122 is lower than the pressure in the inflow-side buffer chamber 134, the check valve 139 opens and the fluid flows into the pump chamber 122 from the inflow-side buffer chamber 134. Also, an inlet connecting tube 136 is provided rising from a lateral surface of the inflow-side block 130. An inflow channel 138 is formed inside the inlet connecting tube 136. The inflow channel 138 opens to the inflow-side buffer chamber 134. The fluid channel 150 shown in FIG. 1 is attached to the inlet connecting tube 136. FIG. 2B shows the shape of the check valve 139, the shape of the reinforcing plate 116 and the like.

Figure 3:
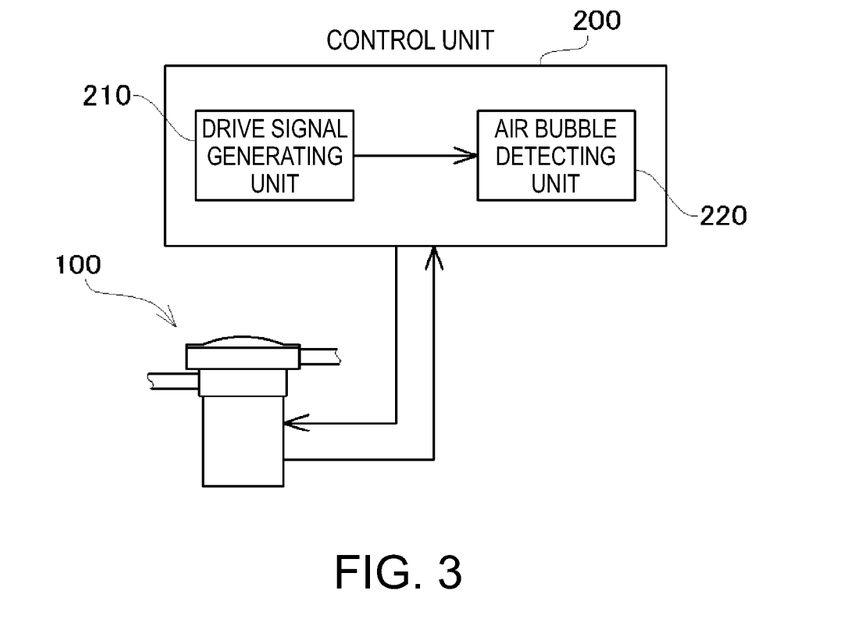
FIG. 3 is an explanatory view showing the configuration of a control unit which controls operations of the fluid feeding pump.

FIG. 3 is an explanatory view showing the configuration of a control unit 200 which controls operations of the fluid feeding pump 100. The control unit 200 of this embodiment includes a drive signal generating unit 210, an air bubble detecting unit 220 and the like. The drive signal generating unit 210 generates a voltage waveform (hereinafter referred to as drive signal) of a positive voltage applied to the piezoelectric element 114 included in the fluid feeding pump 100. The drive signal generated by the drive signal generating unit 210 is amplified by an amplifier (not shown) and subsequently outputted to the fluid feeding pump 100. The drive signal is applied to the piezoelectric element 114 of the fluid feeding pump 100.

At the same time when the drive signal is outputted to the piezoelectric element 114 of the fluid feeding pump 100, a signal (trigger signal) is outputted to the air bubble detecting unit 220 from the drive signal generating unit 210. On receiving the trigger signal, the air bubble detecting unit 220 detects a current flowing through the piezoelectric element 114 and thus detects air bubbles present in the pump chamber 122 of the fluid feeding pump 100. The principle of detecting air bubbles and the detection method will be described in detail later.

The control unit 200 of this embodiment is equivalent to the "drive unit" and the "air bubble determining unit" according to the invention since the control unit 200 applies the drive signal generated by the drive signal generating unit 210 to the piezoelectric element and detects air bubbles in the pump chamber 122.

C. Operations of Fluid Feeding Pump

The fluid feeding pump 100 of this embodiment shown in FIGS. 2A and 2B operates as follows. First, the pump chamber 122, the inflow-side buffer chamber 134, the inflow channel 138, the thin channel 124 and the outflow channel 128 are entirely filled with a fluid. In the state where the drive signal from the control unit 200 is not applied to the piezoelectric element 114, the top surface of the reinforcing plate 116 and the end surface of the piezoelectric element casing 110 are flush with each other. As a positive voltage of a drive signal is applied to the piezoelectric element 114, the piezoelectric element 114 expands and the volume of the pump chamber 122 decreases. The fluid in the pump chamber 122 is thus pressurized. Here, since the check valve 139 is provided between the pump chamber 122 and the inflow-side buffer chamber 134, the fluid in the pump chamber 122 is prevented from flowing back to the inflow-side buffer chamber 134. Consequently, the fluid corresponding to the amount of the decrease in the volume of the pump chamber 122 is fed under pressure from the outflow channel 128.

Next, when the positive voltage applied to the piezoelectric element 114 is eliminated, the piezoelectric element 114 contracts and the volume of the pump chamber 122 returns to the initial volume. The pump chamber 122 now has a negative pressure. This negative pressure acts in a direction in which the fluid in the inflow-side buffer chamber 134 (inflow-side fluid) is sucked into the pump chamber 122, and at the same time, acts in a direction in which the fluid in the outflow channel 128 (outflow-side fluid) is sucked into the pump chamber 122. However, practically, little of the outflow-side fluid is sucked into the pump chamber 122 and mostly the inflow-side fluid is sucked therein. This is because the inertance of the inflow-side channel (the inflow-side buffer chamber 134 and a passage section where the check valve 139 is provided) is considerably smaller than the inertance of the outflow-side channel (thin channel 124 and outflow channel 128).

Inertance is a property value of a channel and indicates the easiness for a fluid to flow when the fluid is about to flow through the channel, triggered by application of pressure at one end of the channel. For example, it is assumed that a channel having a cross-sectional area S and a length L is filled with a fluid (here a liquid) having a density ρ and that a pressure P (to be more precise, the pressure difference P between both ends) is applied to one end of the channel. A force of the pressure P×the cross-sectional area S acts on the fluid in the channel. Consequently, the fluid in the channel starts flowing. If the acceleration of the fluid at this point is a, since the mass of the fluid in the channel is the density ρ×the cross-sectional area S×the length L, an equation of motion can be set up and modified to obtain the following equation.

$$P = \rho \times L \times a. \quad (1)$$

Moreover, if the volumetric flow rate of the flow through the channel is Q and the flow velocity of the fluid flowing through the channel is v, Q=v×S, and therefore the following equation holds.

$$dQ/dt = a \times S \quad (2)$$

As the equation (2) is substituted into the equation (1), the following equation holds.

$$P = (\rho \times L/S) \times (dQ/dt) \quad (3)$$

This equation expresses the equation of motion for the fluid in the channel, using the pressure P applied to one end of the channel (to be more precise, the pressure difference between both ends) and dQ/dt. The equation (3) shows that, with the same pressure P applied, dQ/dt becomes greater (that is, the flow velocity changes greatly) as (ρ×L/S) becomes smaller. This (ρ×L/S) is the value called inertance.

The cross-sectional area S of the channel changes. For example, in the fluid feeding pump 100 of the embodiment shown in FIGS. 2A and 2B, the channel on the side where the fluid flows out of the pump chamber 122 includes two parts with different inside diameters, that is, the thin channel 124 and the outflow channel 128. In the case where the inside diameter of the channel changes in the course, a combined inertance can be employed on the assumption that the channel is divided into plural channels each of which has a constant inside diameter and then the inertances of these channels are combined. The combined inertance can be found similarly to the case where inductances of coils provided in an electric circuit are combined.

In the fluid feeding pump 100 of the embodiment shown in FIGS. 2A and 2B, the combined inertance of the outflow-side channel of the pump chamber 122 is the combination of the inertance of the thin channel 124 and the inertance of the outflow channel 128. Both the thin channel 124 and the outflow channel 128 have a small inside diameter and a long passage length and therefore have a large inertance. The combined inertance resulting from these inertances has a large value. On the other hand, the combined inertance of the inflow-side channel of the pump chamber 122 is the combination of the inertance of the inflow-side buffer chamber 134 and the inertance of the passage section where the check valve 139 is provided.

The inflow-side buffer chamber 134 has a large inside diameter and a short passage length and therefore has a very small inertance. The combined inertance resulting from the combination of the inertance of the inflow-side buffer chamber 134 and the inertance of the passage section where the check valve 139 is provided has a small value. Therefore, as described above, when the pump chamber 122 has a negative pressure, little of the outflow-side liquid with the large combined inertance is sucked and mostly the inflow-side liquid with the small combined inertance is sucked into the pump chamber 122.

In this manner, in the fluid feeding pump 100 of this embodiment, when a positive voltage is applied to the piezoelectric element 114, the fluid in the pump chamber 122 is fed under pressure from the outflow channel 128. As the positive voltage applied to the piezoelectric element 114 is eliminated, the fluid in the inflow-side buffer chamber 134 flows into the pump chamber 122. Therefore, as a positive voltage is applied intermittently to the piezoelectric element 114, the fluid in the pump chamber 122 is repeatedly fed under pressure and the fluid circulates through the fluid channel 150.

Now, as air bubbles enter the pump chamber 122 of the fluid feeding pump 100, the air bubbles are compressed when the volume of the pump chamber 122 is reduced. Therefore, it is difficult to pressurize the fluid sufficiently. Consequently, the fluid cannot be fed under pressure from the outflow channel 128 and the fluid stops circulating. Thus, in order to avoid such a situation, the fluid feeding pump 100 of this embodiment detects air bubbles in the pump chamber 122.

D. Principle of Detecting Air Bubbles

Figure 4A:
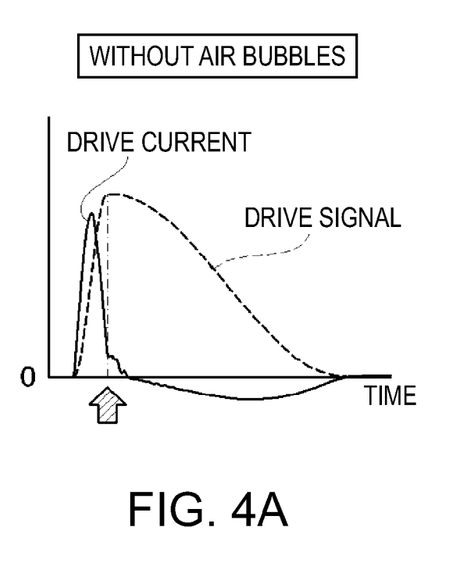
FIGS. 4A and 4B are explanatory views showing a principle according to which the fluid feeding pump of the embodiment detects air bubbles in a pump chamber.
Figure 4B:
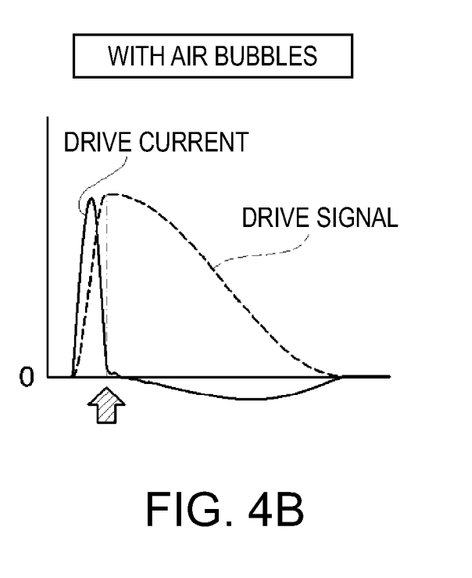

FIGS. 4A and 4B are explanatory views showing the principle that the fluid feeding pump 100 of this embodiment detects air bubbles in the pump chamber 122. FIGS. 4A and 4B show the waveform of a current (drive current) flowing through the piezoelectric element 114 when a drive signal is applied to the piezoelectric element 114. FIG. 4A shows the drive current waveform of the piezoelectric element 114 in the state where there are no air bubbles in the pump chamber 122. FIG. 4B shows the drive current waveform of the piezoelectric element 114 in the state where there are air bubbles in the pump chamber 122.

As shown in FIGS. 4A and 4B, the drive signal applied to the piezoelectric element 114 of the fluid feeding pump 100 of the embodiment includes a former half section where the voltage rises and a latter half section where the voltage falls subsequently. As this drive signal is applied to the piezoelectric element 114, in the state where there are no air bubbles in the pump chamber 122, the current flowing through the piezoelectric element 114 increases and then decreases, but the current does not decrease to 0 at the time point when the drive signal reaches the maximum voltage and then slowly decreases to almost 0, as shown in FIG. 4A. Meanwhile, in the state where there are air bubbles in the pump chamber 122, as the drive signal is applied, the current flowing through the piezoelectric element 114 increases and then decreases, and the current reaches almost 0 at the time point when the drive signal reaches a maximum voltage, as shown in FIG. 4B.

Generally, as can be seen in the state where there are air bubbles (the state of FIG. 4B), the current flowing through the piezoelectric element 114 increases as the applied voltage increases, and the current flowing through the piezoelectric element 114 reaches almost 0 when the drive signal reaches the maximum voltage (when there is no further increase in voltage). However, in the state where there are no air bubbles (the state of FIG. 4A), a phenomenon that the current in the piezoelectric element 114 does not fall to 0 (the current continues flowing) for a whole even after the drive signal reaches the maximum voltage, is observed. This phenomenon can be explained as follows. When a positive voltage is applied to the piezoelectric element 114 and the fluid in the pump chamber 122 is fed under pressure, the piezoelectric element 114 receives a repulsive force from the fluid in the pump chamber 122 and expands less than the originally intended amount of expansion corresponding to the applied voltage. However, when the fluid in the pump chamber 122 is fed under pressure from the outflow channel 128, the fluid in the pump chamber 122 continues flowing to the outflow channel 128 because of the combined inertance of the thin channel 124 and the outflow channel 128, and the pressure in the pump chamber 122 decreases. Therefore, the piezoelectric element 114 expands to the originally intended amount of expansion and a piezoelectric effect causes the current to flow through the piezoelectric element 114 even when there is no further voltage increase in the drive signal. Thus, by using the air bubble detecting unit 220 to detect a change in the drive current waveform due to such a phenomenon, air bubbles in the pump chamber 122 can be detected.

E. FIRST EXAMPLE

Figure 5:
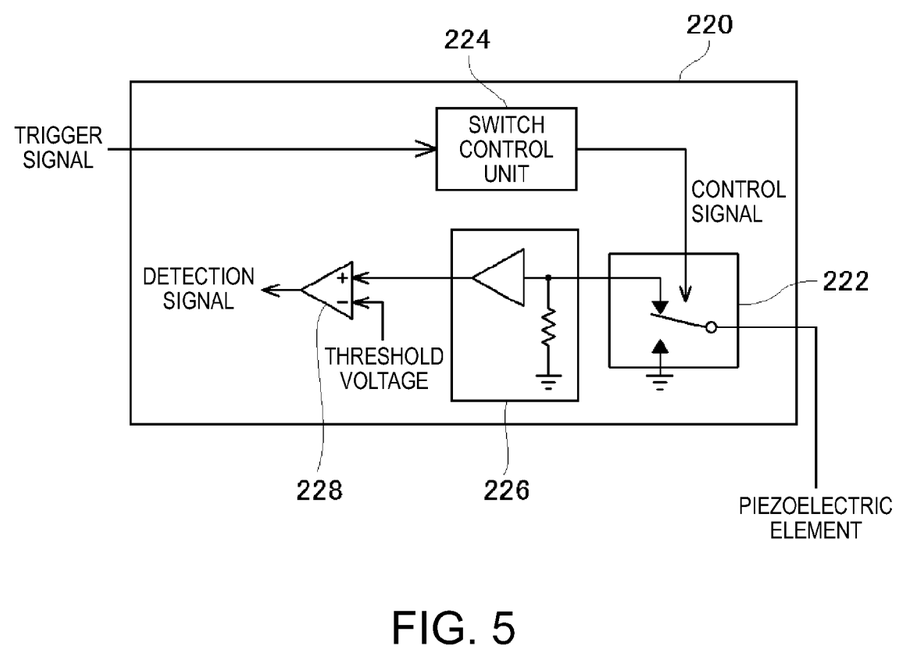
FIG. 5 is an explanatory view showing the inner configuration of an air bubble detecting unit according to a first example.

FIG. 5 is an explanatory view showing the inner configuration of the air bubble detecting unit 220 according to a first example. As shown in FIG. 5, the air bubble detecting unit 220 of the first example is configured with electric circuits including a switch unit 222, a switch control unit 224, a current detecting unit 226, a comparator unit 228 and the like.

The piezoelectric element 114 of the fluid feeding pump 100 is connected to the switch unit 222 of the air bubble detecting unit 220. The switch unit 222 is formed mainly by an analog switch and the switch changes over between ON and OFF under the control of the switch control unit 224. In the switch unit 222, the switch is usually ON in response to a Hi-state control signal from the switch control unit 224. Therefore, the piezoelectric element 114 and the current detecting unit 226 are connected with each other. Meanwhile, as a trigger signal from the drive signal generating unit 210 is inputted to the switch control unit 224, the control signal from the switch control unit 224 turns into a Low-state for a predetermined period and the switch turns OFF. The piezoelectric element 114 and the current detecting unit 226 are thus disconnected from each other.

The current detecting unit 226 is formed as a circuit including a resistor. In this current detecting unit 226, a current flowing through the piezoelectric element 114 is detected as a voltage corresponding to the magnitude of the current, in the state where the piezoelectric element 114 and the current detecting unit 226 are connected with each other.

The voltage thus detected by the current detecting unit 226 is outputted to the comparator unit 228. The comparator unit 228 is formed mainly by an IC chip. The comparator unit 228 compares the voltage inputted from the current detecting unit 226 with a preset threshold voltage and outputs either Hi or Low voltage state according to the result of the comparison. In this example, when the voltage inputted from the current detecting unit 226 is greater than the threshold voltage, a Hi voltage state is outputted as a detection signal. When the inputted voltage is smaller than the threshold voltage, a Low voltage state is outputted as a detection signal.

Figure 6A:
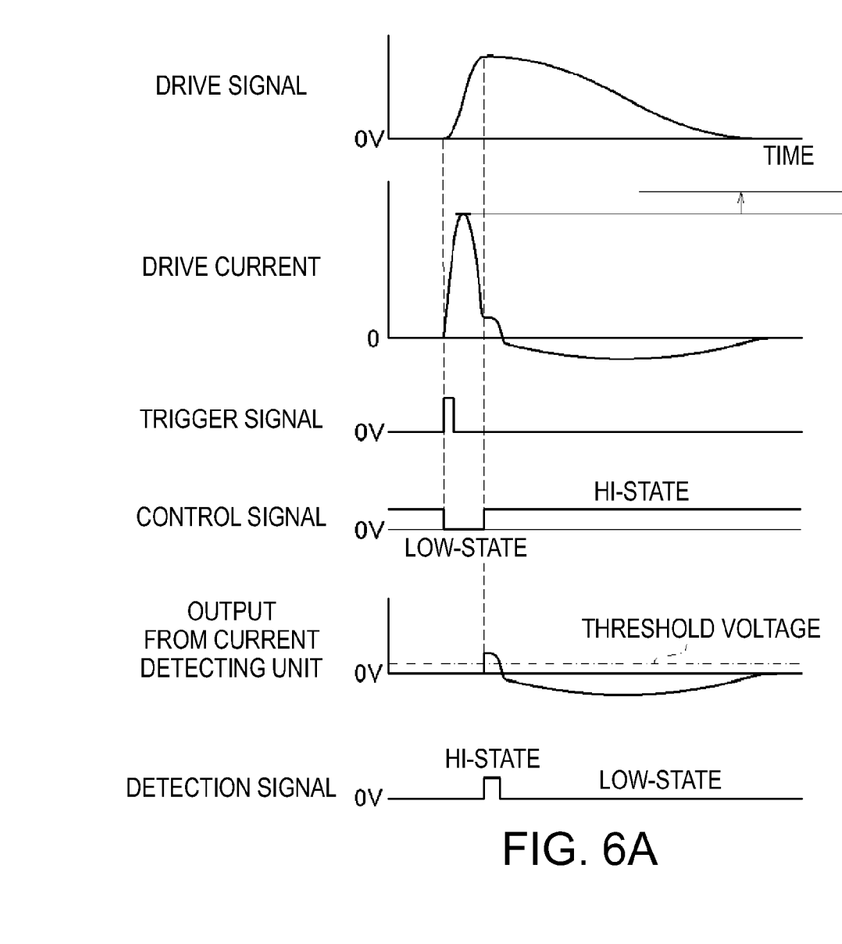
FIGS. 6A and 6B are explanatory views illustrating how the air bubble detecting unit of the first example detects air bubbles.
Figure 6B:
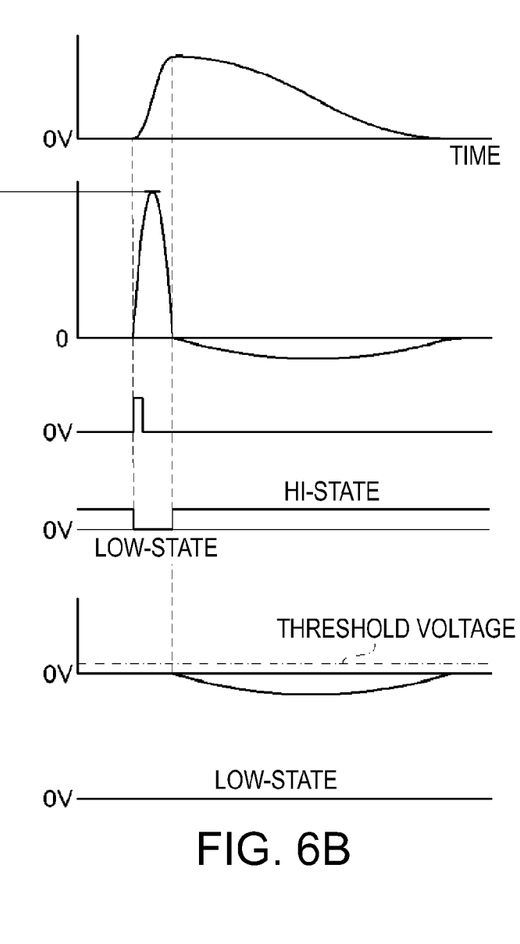

FIGS. 6A and 6B are explanatory views showing how the air bubble detecting unit 220 of the first example detects air bubbles. At the top of FIGS. 6A and 6B, a drive signal applied to the piezoelectric element 114 is shown, and below the drive signal, a drive current waveform in the piezoelectric element 114 when the drive signal is applied is shown. FIG. 6A shows the drive current waveform when there are no air bubbles in the pump chamber 122. FIG. 6B shows the drive current waveform when there are air bubbles.

Below the drive current waveforms, a trigger signal outputted from the drive signal generating unit 210 is shown. As shown in FIGS. 6A and 6B, the drive signal generating unit 210 outputs the trigger signal at the time point when the application of the drive signal to the piezoelectric element 114 is started. Below the trigger signal, a control signal from the switch control unit 224 is shown. The control signal turns to Low-state as the switch control unit 224 receives the trigger signal. The control signal returns to Hi-state again after the lapse of a predetermined period.

The predetermined period during which the control signal is Low-state is set to a period from when the applicant of the drive signal to the piezoelectric element 114 is started to when the drive signal reaches a maximum voltage. When the control signal is Low-state, the switch unit 222 is OFF. Therefore, during the predetermined period, the current in the piezoelectric element 114 (to be more precise, the voltage corresponding to the magnitude of the current) is not detected by the current detecting unit 226. Consequently, as shown in FIGS. 6A and 6B, the drive current waveform excluding the waveform corresponding to the period from the start of the application of the drive signal to the reaching to the maximum voltage is taken out and outputted from the current detecting unit 226.

The relation in terms of magnitude between the output from the current detecting unit 226 thus obtained and a preset threshold voltage is detected using the comparator unit 228. In FIGS. 6A and 6B, the threshold voltage to be compared with the output from the current detecting unit 226 is shown by a chain dotted line. Below the output from the current detecting unit 226, an output (detection signal) from the comparator unit 228 is shown.

When there are no air bubbles in the pump chamber 122, the current continues flowing through the piezoelectric element 114 for a while even after the drive signal reaches the maximum voltage. Therefore, the output waveform from the current detecting unit 226 has a portion where the voltage is higher than 0 V (see FIG. 6A). Since the threshold voltage in this example is set to a slightly higher value than 0 V, a detection signal of Hi-state is outputted from the comparator unit 228 during the period when the output from the current detecting unit 226 is higher than the threshold voltage. In response to this Hi-state detection signal, the air bubble detecting unit 220 determines that there are no air bubbles in the pump chamber 122. On the other hand, in the case where there are air bubbles, since the current in the piezoelectric element 114 is already reduced to almost 0 when the maximum voltage is applied, the output waveform from the current detecting unit 226 rarely has a portion where the voltage is higher than 0 V (see FIG. 6B). Therefore, the output voltage from the comparator unit 228 keeps Low-state. In response to this, the air bubble detecting unit 220 determines that there are air bubbles.

When the air bubble detecting unit 220 determines that there are air bubbles in the pump chamber 122, the control unit 200 turns on a warning lamp (not shown) provided in the fluid feeding pump 100 and thus prompts the user to carry out a maintenance work to remove air bubbles.

With the air bubble detection method of this first example, air bubbles in the pump chamber 122 can be detected, using the piezoelectric element 114 for pressurizing the fluid in the pump chamber 122. Thus, since a separate device for detecting air bubbles need not be provided in the fluid feeding pump 100, the fluid feeding pump 100 can be small-sized.

As shown in FIGS. 6A and 6B, the peak value of the drive current waveform increases when there are air bubbles in the pump chamber 122. Therefore, it is also possible to detect air bubbles by detecting the increase in the peak value of the drive current waveform. However, the peak value of the drive current waveform varies according to the amplitude of the drive signal applied to the piezoelectric element 114. Therefore, whether the peak value of the drive current waveform is high or low must be determined according to the drive signal that is applied and the accuracy of the determination is largely influenced by whether an appropriate threshold value can be set or not.

To cope with this, in the air bubble detection method of this example, air bubbles are detected based on whether the current continues flowing through the piezoelectric element 114 or not, despite that the drive signal reaches the maximum voltage and the voltage stops increasing. Whether the current continues flowing or not can be determined without being influenced by the setting of the threshold value. Therefore, whether there are air bubbles or not can be detected accurately.

F. SECOND EXAMPLE

The above-described air bubble detecting unit 220 of the first example is described as detecting whether there is a current flowing through the piezoelectric element 114 or not after the application of the maximum voltage in order to detect a change of the drive current waveform in the piezoelectric element 114 after the drive signal reaches the maximum voltage. Here, to detect a change of the drive current waveform, the amplitude of a specific frequency component of the drive current waveform may be detected.

Figure 7:
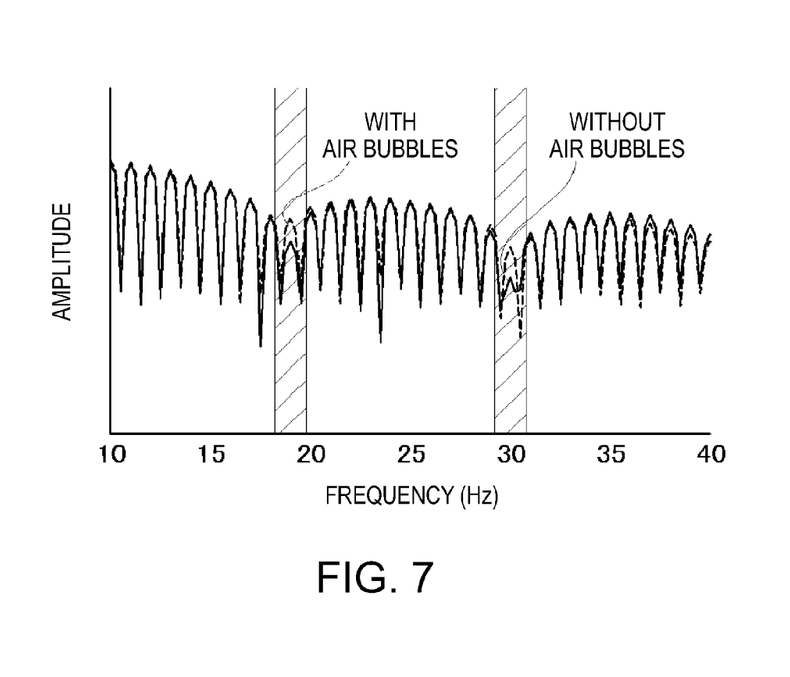
FIG. 7 is an explanatory view showing the result of a spectral analysis of a drive current waveform when a drive signal is applied to a piezoelectric element.

FIG. 7 is an explanatory view showing the result of a spectral analysis of the drive current waveform when the drive signal is applied to the piezoelectric element 114. In FIG. 7, a solid line shows the result of the spectral analysis of the drive current waveform in the case where there are no air bubbles in the pump chamber 122, and a broken line shows the result of the analysis in the case where there are air bubbles.

As shown in FIG. 7, comparing the case where there are no air bubbles in the pump chamber 122 and the case where there are air bubbles, the amplitude of specific frequency components (19 Hz component and 30 Hz component) of the drive current waveform is greater in the case where there are air bubbles. Since a change of the drive current waveform appears as a change in the amplitude of specific frequency components in this manner, whether there are air bubbles or not is determined by detecting the amplitude of either the 19 Hz or 30 Hz frequency component.

Figure 8:
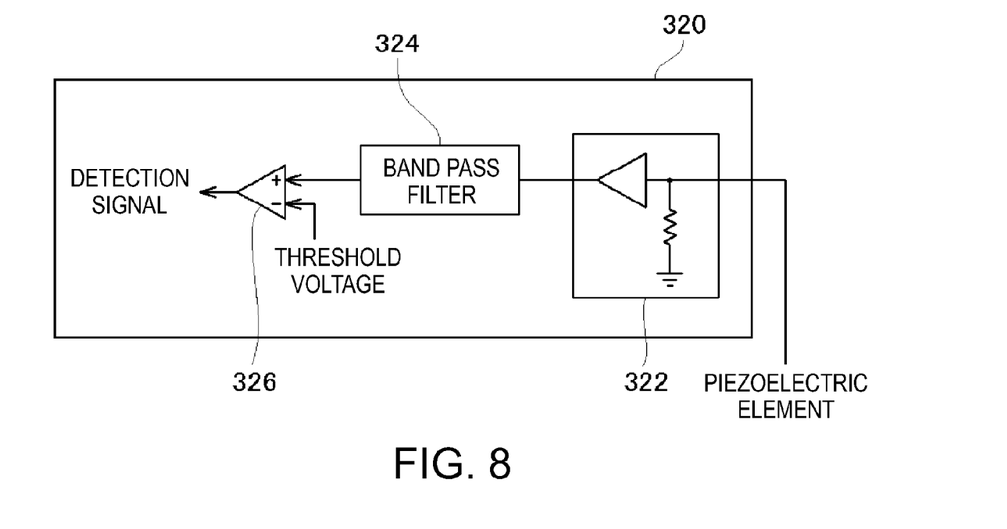
FIG. 8 is an explanatory view showing the inner configuration of an air bubble detecting unit according to a second example.

FIG. 8 is an explanatory view showing the inner configuration of an air bubble detecting unit 320 according to a second example. As shown in FIG. 8, the air bubble detecting unit 320 of the second example includes a current detecting unit 322 connected to the piezoelectric element 114, a band pass filter 324 which takes out a predetermined frequency component (in the second example, a 19 Hz frequency component) from an output from the current detecting unit 322, a comparator unit 326 which compares an input from the band pass filter 324 with a threshold voltage and outputs a Hi-state detection signal when a higher voltage than the threshold voltage is inputted, and so on.

Figure 9A:
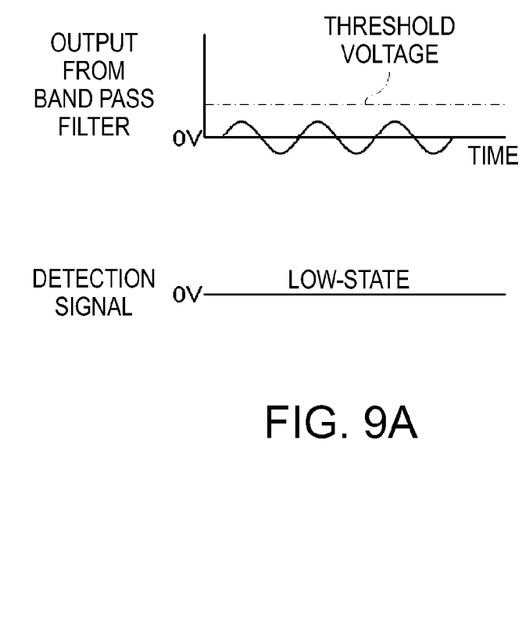
FIGS. 9A and 9B are explanatory view illustrating how the air bubble detecting unit of the second example detects air bubbles.
Figure 9B:
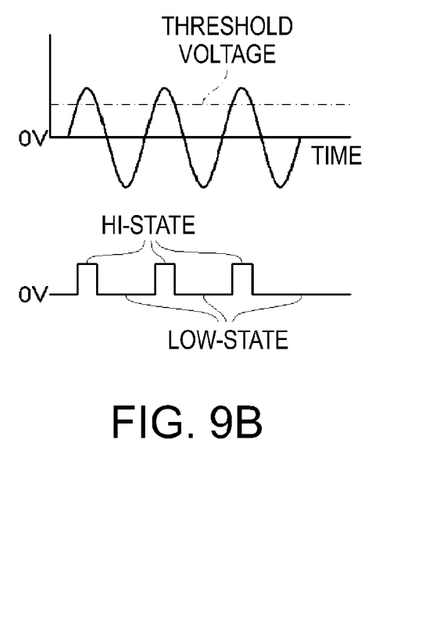

FIGS. 9A and 9B are explanatory views showing how the air bubble detecting unit 320 of the second example detects air bubbles. At the top of FIGS. 9A and 9B, an output from the band pass filter 324 (corresponding to the 19 Hz frequency component of the drive current waveform) is shown. At the bottom of FIGS. 9A and 9B, an output from the comparator unit 326 (detection signal) is shown. FIG. 9A shows the output in the state where there are no air bubbles in the pump chamber 122. FIG. 9B shows the output in the state where there are air bubbles.

When there are no air bubbles in the pump chamber 122, the output from the band pass filter 324 has a small amplitude and therefore the output does not exceed the threshold voltage of the comparator unit 326. Therefore, a Low-state detection signal continued being outputted from the comparator unit 326. In this case, the air bubble detecting unit 320 determines that there are no air bubbles in the pump chamber 122. Meanwhile, when there are air bubbles, since the amplitude of the output voltage from the band pass filter 324 increases and exceeds the threshold voltage, a Hi-state detection signal is outputted from the comparator unit 326 during the period when the output voltage exceeds the threshold voltage. Receiving such a detection signal, the air bubble detecting unit 320 determines that there are air bubbles in the pump chamber 122.

The above-described air bubble detecting unit 320 of the second example can detect air bubbles in the pump chamber 122 without being controlled by an external signal (trigger signal) like the air bubble detecting unit 220 of the first example. Therefore, the control for detecting air bubbles can be simplified.

The fluid feeding pump 100 of the embodiment and the cooling device 10 equipped with the fluid feeding pump 100 are described above. However, the invention is not limited to all the above embodiment and examples and can be carried out in various forms without departing from the scope of the invention. For example, in the examples, the air bubble detecting units 220, 320 are applied to the fluid feeding pump 100 which circulates a fluid. However, the air bubble detecting units 220, 320 can also be applied to a device which ejects a fluid, based on a similar mechanism to the fluid feeding pump 100.

Figure 10:
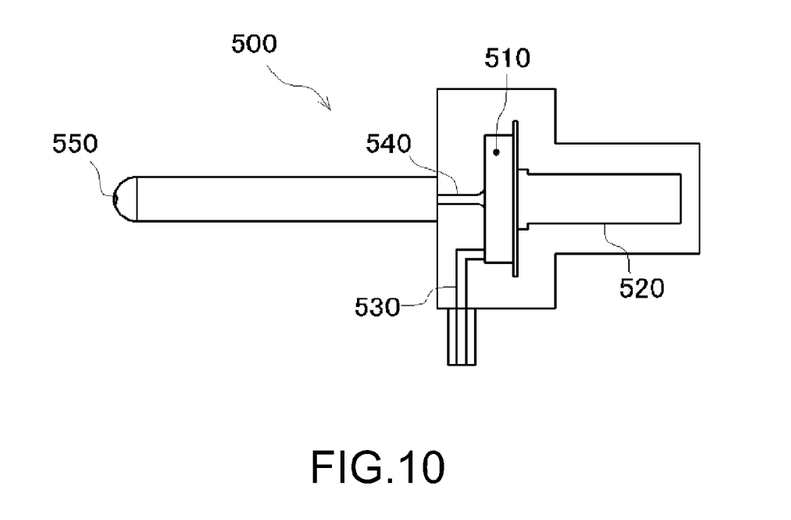
FIG. 10 is an explanatory view showing an excision device which excises a living tissue or the like, using the pressure of an ejected fluid, as another example of a device to which the air bubble detecting unit can be applied.

FIG. 10 shows an excision device 500 which excises a living tissue or the like, using the pressure of an ejected fluid, as another example of a device to which the air bubble detecting units 220, 320 can be applied. The excision device 500 roughly includes a pump chamber 510, a piezoelectric element 520 for varying the volume of the pump chamber 510, an inflow channel 530 which supplies a fluid to the pump chamber 510, a fluid ejection opening 550 from which the fluid in the pump chamber 510 is ejected outside via an outflow channel 540, and so on. Also in such an excision device 500, the fluid is fed under pressure from the pump chamber 510 based on a similar mechanism to the foregoing fluid feeding pump 100, and whether there are air bubbles in the pump chamber 510 or not needs to be detected in order to avoid an inability to feed the fluid under pressure due to the presence of air bubbles. Therefore, by applying the air bubble detecting units 220, 320 of the examples to the excision device 500, similar advantageous effects to the case where the air bubble detecting units 220, 320 are applied to the fluid feeding pump 100 can be achieved.

This application claims priority to Japanese Patent Application No. 2011-186963, filed on Aug. 30, 2011, the entirety of which is hereby incorporated by reference.

What is claimed is:

1. A fluid feeding pump which varies a volume of a pump chamber and thus feeds a fluid out of the pump chamber, the fluid feeding pump comprising:
a piezoelectric element which accumulates electric charges inside when a voltage is applied, and which deforms according to an amount of accumulated electric charges and thus increases or decreases the volume of the pump chamber;

a drive unit which applies a drive signal with a waveform increasing to a predetermined maximum voltage and then decreasing, and thus drives the piezoelectric element; and an air bubble determining unit which detects a current flowing through the piezoelectric element within a predetermined period after the drive signal is applied to the piezoelectric element, and thus determines whether there is an air bubble in the pump chamber or not, wherein the air bubble determining unit determines that there is an air bubble in the pump chamber when the detected current is smaller than a threshold.

2. The fluid feeding pump according to claim 1,
wherein the predetermined period is a period from when the drive signal reaches the maximum voltage to when the application of the drive signal to the piezoelectric element is started after the drive signal reaches the maximum voltage, or a period after the drive signal reaches the maximum voltage to when the application of the drive signal to the piezoelectric element is started after the drive signal reaches the maximum voltage, wherein the air bubble determining unit is disconnected during at least a portion of the drive signal.

3. The fluid feeding pump according to claim 1,
wherein the drive signal is applied to the piezoelectric element to discharge the fluid from the pump chamber.

4. A medical apparatus comprising the fluid feeding pump according to claim 1.

5. A medical apparatus comprising the fluid feeding pump according to claim 2.

6. A medical apparatus comprising the fluid feeding pump according to claim 3.

7. An air bubble determination method for a pump, the pump including
a piezoelectric element which accumulates electric charges inside when a voltage is applied, and which deforms according to an amount of accumulated electric charges and thus increases or decreases a volume of a pump chamber, and a drive unit which applies a drive signal with a waveform increasing to a predetermined maximum voltage and then decreasing, and thus drives the piezoelectric element, wherein the pump feeds a fluid by varying the volume of the pump chamber, the method comprising:
detecting a current flowing through the piezoelectric element within a predetermined period after the drive signal is applied to the piezoelectric element; and determining there are air bubbles in the pump chamber when the detected current is smaller than a threshold.

8. The air bubble determining method according to claim 7, further comprising:
disconnecting the air bubble determining unit during at least a portion of the drive signal, wherein the predetermined period is a period from when the drive signal reaches the maximum voltage to when the application of the drive signal to the piezoelectric element is started after the drive signal reaches the maximum voltage, or a period after the drive signal reaches the maximum voltage to when the application of the drive signal to the piezoelectric element is started after the drive signal reaches the maximum voltage, and detecting a current flowing through the piezoelectric element within the predetermined period after the drive signal is applied to the piezoelectric element after connecting the piezoelectric element to the air bubble determining unit.

9. The air bubble determining method according to claim 7, wherein the drive signal is applied to the piezoelectric element to discharge the fluid from the pump chamber.

* * * * *